United States Patent [19]

Hignett et al.

[11] Patent Number: 4,536,313
[45] Date of Patent: Aug. 20, 1985

[54] PEROXYGEN COMPOUND

[75] Inventors: Geoffrey J. Hignett, Lymm; Kenneth T. Rowbottom; William R. Sanderson, both of Warrington, all of England

[73] Assignee: Interox Chemicals Limited, London, England

[21] Appl. No.: 588,817

[22] Filed: Mar. 12, 1984

[30] Foreign Application Priority Data

Mar. 15, 1983 [GB] United Kingdom ............... 8307037

[51] Int. Cl.³ .................. C11D 7/54; C11D 3/395; C07C 179/133; C07C 133
[52] U.S. Cl. ..................................... 252/100; 8/111; 252/94; 252/95; 260/502 R; 260/505 E; 514/568; 568/558
[58] Field of Search ............... 8/111; 252/94, 95, 100; 260/502 R, 505 E; 424/338; 568/558

[56] References Cited

U.S. PATENT DOCUMENTS 2,058,315 10/1936 Huttenlocher et al. ......... 260/502 R
3,143,562 8/1964 Silbert et al. ...................... 260/465
4,259,201 3/1981 Cockrell, Jr. et al. ................ 8/111
4,403,994 9/1983 Hignett ............................ 568/558

OTHER PUBLICATIONS

Bachhawat et al., "Epoxidation and Trans-hydroxylation of Olefins with O-Sulfoperbenzoic Acid", Tetrahedron Lett. 1971, (8), 691–692 (CA 74: 125056g).

Primary Examiner—Paul Lieberman
Assistant Examiner—Robert A. Wax
Attorney, Agent, or Firm—Larson and Taylor

[57] ABSTRACT

Increased energy costs have stimulated a demand for peroxygen compounds that are effective at ambient to hand-hot temperatures, but peroxyacids and acyl peroxides tend to suffer from one or more of poor thermal stability, or sensitivity to impact, thereby rendering their manufacture or storage hazardous, or from poor solubility. The instant invention provides a salt of the formula (in anhydrous form):

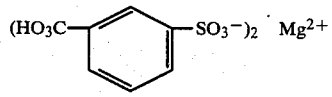

The salt can be incorporated in low temperature bleaching compositions, in washing compositions, in sanitizing compositions or in disinfection/sterilization compositions.

23 Claims, No Drawings

PEROXYGEN COMPOUND

The present invention relates to peroxygen compounds, and more particularly to a salt of an organic peroxyacid. The present invention also relates to compositions containing such a salt, and the uses of such a salt and compositions in cleaning, bleaching or disinfection.

For many years, it has been common for any washing or disinfecting compositions for the European market to contain a peroxygen compound, which can act as an oxidising agent, a bleach and to at least some extent a disinfectant. Particularly for washing or bleaching compositions, the peroxygen compound has typically been a particulate alkali metal persalt such as sodium perborate tetrahydrate or sodium percarbonate which generates hydrogen peroxide in aqueous solution. Similarly, in America, peroxygen compound-containing additives often in tablet form are widely available for use in conjunction with other washing compositions. Such persalts function most effectively at temperatures in excess of 80° C., but in recent years there has been a trend towards the use of synthetic fibres for apparel and household textile wares which may themselves or their finishes or dyes be adversely affected by exposure to high washing temperatures, and accordingly, increasing interest is being shown in washing at lower temperatures, for example in the range of ambient to 60° C. Interest has been further intensified by substantial increases in the cost of energy since the mid 1970's. For a peroxygen compound to be effective at such lower temperatures, it is necessary for it to be more active than the aforementioned persalts, and accordingly considerable research effort has been directed by many organisations to locate either more active peroxygen compounds or compounds which can be added to persalts in order to activate them. Both approaches suffer from their own disadvantages. The use of activators can be hindered by segregation of them from persalt during storage or transportation thereby leading to inconsistent washing performance, the need for both components to be dissolved simultaneously during the washing performance can lead to incomplete development of the active system during the restricted washing period available in most washing machines, and many can interact destructively with various other components in washing compositions. On the other hand, the more active peroxygen compounds are not without problems. First, many of them are comparatively unstable, even when stored alone, and this instability is compounded by formulation with the rest of the washing compositions, and that many of such compounds are somewhat hazardous to handle, being sensitive to thermal shock, impact or other disturbance. In view of the problems associated with the existing active systems, there is a continuing need for alternatives having advantageous combinations of properties to be located.

In British Patent Specification No. 1368400, Procter and Gamble disclose bleaching compositions containing an organic peroxyacid having the generally formula $HCO_3-R-Y$, in which R is selected from, inter alia, arylene groups containing from 6 to 8 carbon atoms and Y is selected from inter alia groups providing in aqueous solution an anionic moiety attached to R, and water soluble salts of the organic peroxyacids. Examples of groups which provide an anionic moiety in aqueous solution include $-CO_2H$, $-CO_3H$, $-SO_3H$, and $SO_4H$. The aromatic nuclei of such peroxygen compounds can be substituted by any non-interfering substituent such as halogen groups. Although reference is made in generalised terms to the provision of water soluble salts of the organic peroxyacids, no such salts were actively tried and tested, and the only salts named were the sodium and potassium salts of diperazelaic acid and diperadipic acid as well as the monosodium salt of diperoxyterephthalic acid. Of these salts, no reference has been found in the literature to other than the sodium salt of diperoxyterephthalic acid, and even this salt was rated as very hazardous. Even if they could be isolated, the specified salts of diperazelaic and diperadipic acids would be exceedingly hazardous when measured by either the impact test, or the thermal stability test. Accordingly, the said Procter and Gamble patent, and the many others by them that use the same or similar text in respect of organic peroxyacids and salts thereof, provide no functional teaching as to which salts of peroxyacids to use.

Many years ago, Huttenlocher and Lamatsch indicated in U.S. Pat. No. 2,058,315 the formation of various salts of aromatic persulphuric acids, including salts of toluene and napthalene persulphuric acids. Unfortunately, present day IR and chemical analysis shows that the napthalene-based salts are hydrogen peroxide adducts rather than peracids; so that the teaching of this specification is open to doubt. Secondly, and perhaps more importantly, even though the toluene perssulphuric acid salt appears to be a peracid salt, when its stability was measured under normal test conditions (30° C., relative humidity constant at levels from 7 to 96%), it lost at least 60% of its initial available oxygen in a week. Accordingly, this specification provides no reliable teaching as to the fitness of various peracid salts for incorporation in bleaching or detergent compositions.

Accordingly, it is an object of the present invention to provide in solid form a salt which upon dissolution in aqueous media generates a peroxyacid and which does not require excessive desensitisation to enable it to be stored or transported. It is a further objective to provide bleaching, oxidising, or disinfecting compositions containing such a salt, in some embodiments. It is a yet further object of other embodiments of the invention to provide processes for oxidising, bleaching or disinfecting, especially at ambient temperature to around 60° C. Other and additional objects of the present invention will be apparent from the detailed description of the invention below.

According to a first aspect of the present invention, there is provided in solid form, a salt, expressed in anhydrous form, having the general formula:

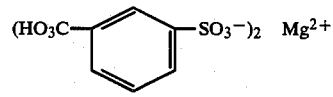

It will be recognised that the salt is formed from the sulphonate group and that the percarboxylic acid group remains in acid form. For convenience, the salt may be referred to herein as MMSPB.

Although it is possible to propose many theoretical structures for substituted peroxybenzoic acid salts, it will be recognised upon practical evaluation that various of them lack one or more essential characteristics. Thus, for example, peroxybenzoic acids substituted around the benzene nucleus by one sulphonate group can theoretically exist as ortho meta and para isomers. There are wide and unpredictable differences between the isomers. The ortho salts have demonstrated such poor performance in e.g. washing trials that they lack applicability to washing and/or disinfection. Various of the para salts demonstrated poor resistance to shock. Finally, with specific respect to the meta salts, it has not been possible, so far, to make salts other than the magnesium salt in solid form.

In a second aspect of the present invention, there is provided a process for the manufacture of the monomagnesium salt of 3-sulphoperoxybenzoic acid comprising the step of reacting a suspension of the corresponding salt of 3-sulphobenzoic acid or salt thereof in the presence of a strong acid with concentrated hydrogen peroxide until at least some of the carboxylic acid groups have been peroxidised at a temperature selected in the range of ambient temperature to 60° C., subsequently cooling the reaction mixture, and/or, augmenting the concentration of metal ions in solution by introduction thereinto of a saturated aqueous solution of magnesium nitrate to the extent necessary for a precipitate to form, and separating the precipitate from its mother liquor.

The starting material can be 3-sulphobenzoic acid, or a water-soluble salt thereof, of which one of the most convenient is the sodium salt.

The strong acid employed in the peroxidation reaction is typically methane sulphonic acid, or any acid having approximately comparable or even higher acid strength. Such alternative acids include sulphuric acid or a mixture thereof with methanesulphonic acid and optionally the strong acid can comprise or include phosphoric acid.

The peroxidation reaction needs only a catalytic amount of strong acid, such as of the order of 0.001 moles per mole of 3-sulphobenzoic acid but where a salt of that acid is used, it is preferable to use at least a stoichiometric amount of strong acid. It is highly preferable to employ no more than 20 moles of strong acid per mole of 3-sulphobenzoic acid in order to enable to subsequent solid formation step to proceed readily, and indeed a practical ratio is often within the range of 5:1 to 10:1.

The reaction medium can contain a non-reactive liquid organic solvent, which in practice is usually a hydrocarbon, chlorinated hydrocarbon or mixture thereof. For convenience, it is most desirable to select as solvent one or a mixture that has a boiling point within the temperature range specified herein, and particularly from 30° to 45° C. Especially suitable solvents include pentane and dichloromethane, which boil at about 40° C.

The concentrated hydrogen peroxide is typically employed in a concentration of at least 60 and generally at least 70% w/w and preferably in a mole ratio to the non-peroxygenated compound of at least 1 mole per mole of the latter.

It will be recognised that there are various ways that are suitable for bringing the solid compound into contact with the hydrogen peroxide. The hydrogen peroxide can be introduced gradually into a body of the suspension of compound in the strong acid-containing medium, or vice versa, or the solid compound into a solution of the hydrogen peroxide, or they can be introduced simultaneously or alternately into a body of the reaction mixture, and after a suitable reaction period the solid product is separated from the mother liquor. Alternatively, the two reagents can be introduced in regulated fashion into the body of the reaction mixture either continuously or intermittently and when the reagents have been introduced in an appropriate mole ratio a proportion of the body can be withdrawn continuously or intermittently as desired for product recovery therefrom. The rate of introduction of the reagents and rate of removal of reaction mixture from the body is desirably balanced so as to provide a residence time within the range given hereinafter. In other variations, the mother liquor from which product has been removed can be recycled and this can be employed in whole or in part as the process operator so desires, together with any fresh solvent, hydrogen peroxide and non-peroxygenated compound needed to sustain the cycle. Many variations in the manner of introduction of the reagents, solvent and any recycled mother liquor into the reaction vessel can be made. Examples include the premixing of all or part of one reagent, e.g. the non peroxygenated salt, with recycle mother liquor and/or fresh solvent, premixing all or part of the other reagent with the other of the mother liquor or fresh solvent, and at the other extreme is the separate and simultaneous or phased introduction of all of the reagents, solvent and any recycled mother liquor. Intermediate variations are permissible also. It will be recognised that such variations are within the capability of practising Chemical Engineers, and require no further clarification.

The mole ratio of hydrogen peroxide to non-peroxygenated sulphobenzoic acid compound is generally selected in the range of from 1:1 to 10:1 and in many embodiments from 1.2:1 to 5:1. Naturally, any residual hydrogen peroxide in the mother liquor after separation from the peroxygenated salt is normally taken into account in determining the amount of fresh hydrogen peroxide that should be added to restore its concentration to its original level for reaction with further non-peroxygenated compound. Such residual hydrogen peroxide can often be obtained by employing an initial mole ratio of at least 2:1.

Conveniently, there is no need for the reaction to be carried out at a temperature in excess of about 60° C. and it is preferred on general safety grounds to operate at a temperature of not above 50° C. Naturally, the reaction period, or the corresponding residence time in a continuous process, is increased at lower reaction temperatures in order to ensure that a given proportion of the salt is peroxygenated. For convenience it is preferred not to exceed a reaction period/residence time of 10 hours and in fact the reaction temperature is within the region of 30° C. to 45° C., so that a reaction period/residence time selected within the range of half an hour to 4 hours enables substantially complete peroxygenation to occur.

The resultant peroxygenated salt has been found to be very soluble in aqueous media, and accordingly its isolation from the reaction mixture is markedly assisted by the step of enforced cooling, preferably reducing the temperature of the reaction mixture by at least 15° C. and is especially helped by the introduction of saturated magnesium nitrate salt into solution. One particularly convenient form in which to introduce it is as a substantially saturated solution in chilled water but introduction as a suspension or even in particulate form can be contemplated alternatively. The magnesium salt of the 3-sulphoperoxybenzoic acid precipitates from the reaction mixture and this precipitate can subsequently be washed, preferably with a saturated magnesium nitrate solution.

In one particularly convenient preparation, the 3-sulphobenzoic acid can be obtained by sulphonation of benzoic acid using at least 3.5 moles of sulphuric acid per mole of benzoic acid at about 200° C. and the resultant product used in the peroxidation step, providing naturally that no more than 20 moles per mole of 3-sulphobenzoic acid is present.

Of considerable importance for a peroxygen compound is its thermal stability. As a general rule peroxyacids have poor stability, e.g. monoperoxysuccinic acid has an S.A.D.T. of only 38/40° C. and diperoxydodecanedioic acid, similarly, when calculated at the 25 kg container scale, thereby rendering summer storage of such compounds undesirable. However, MMSPB is well above this range, in that it yielded no exotherm at up to 80° C. as measured by accelerated rate calorimetry, so that the compound can readily be transported/stored even in hot climates. Consequently there is no need to take precautions to control the exotherm, such as the incorporation of substantial proportions of various acids like maleic acid or boric acid.

A second aspect of practical importance is the impact sensitivity of any peroxygen compound. For peroxyacids MMSPB has an acceptable resistance to impact, although it would be preferable to decrease its sensitivity somewhat more with diluents.

Where it is desired to desensitise the MMSPB, this can readily be effected by bringing the salt into intimate contact with a desensitising amount of a diluent, such an amount normally being at least half the weight of MMSPB. Once the salt has been desensitised, any further diluent is at the discretion of the formulator. It is usual for the desensitised composition to have an avox of at least 0.5% w/w which corresponds to a minimum MMSPB content in the desensitised composition of 7%, approximately, and in practice it is often preferable for the concentration of the salt to be selected within the range of 10 to 50% for MMSPB.

One class of desensitising diluents comprises alkali metal or alkaline earth metal salts of halogen-free acids and especially of strong acids. In particular such diluents salts, are often sodium, potassium, or magnesium salts especially of sulphate compound by sulphate or mixtures thereof ortho, pyro or polyphosphates or mixtures thereof organic acids including $C_8$ to $C_{20}$ mono basic or dibasic acids and aromatic acids in which the benzene nucleus is subsituted by at least one carboxylic acid group and if desired one or more lower alkyl such as methyl, or sulphonate groups. Additionally, all or part of the aliphatic or aromatic acids can be present in acidic form, insofar as they are solid in use.

Other suitable inorganic diluents include boric acid and alkaline earth metal borates, solid aluminium salts sodium carbonate and/or bicarbonate including natural or synthetic zeolites and clays, and various hydrogen peroxide-developing persalts such as sodium perborate or sodium percarbonate.

Other organic diluents include hydrocarbon waxes, $C_1$-$C_6$ esters of aromatic acids especially of phthalic acid and solid dextrins, gelatines and starches. The MMSPB can be diluted using various techniques such as simply admixture, possibly followed by tabletting or enclosure within a pouch or other enclosure which either ruptures or is penetrated in use, or is removed, or ruptured before use by the user. Other suitable techniques include agglomeration, granulation, pelletisation, formation of noodles or granulates or alternatively accommodation of two or more of the foregoing techniques. Alternatively or additionally, at least part of the diluent may comprise a film-forming substance such as aliphatic fatty acid amides or esters, fatty alcohol polyglycol ethers, polyethylene glycol or fatty acid or amide derivatives thereof, and esters and amides of polyols such as glycerol or sorbitol and ethoxylated derivatives thereof. Such coatings can perform the dual function of dilution and isolating the peroxyacid from other components of compositions with which it may be mixed subsequently, and of course preformed granulates, agglomerates, or extrudates containing either the particulates MMSPB alone or with one or more of the non-film forming diluents can also be coated.

It will be recognised that various of the aforementioned diluents are valued components in their own right of washing compositions or bleaching compositions or disinfectant compositions, for example, those compounds which act either as builders or as pH regulators or those salts which can lose water of hydration, or boric acid are exotherm control agents. It will therefore be recognised that the incorporation of such dual or even triple function diluents in the composition in the appropriate amounts can lead to the generation of aqueous solutions either of the composition by itself or in the presence of some other compositions such as a washing composition having a pH within a wide range from mildly acidic through neutral to moderately alkaline by the use of respectively acids and bases or alkaline buffers in varying ratios with each other and with the MMSPB. Naturally, the higher proportion of acids such as boric acid or organic acids or zeolites in acid form tend to produce less alkaline solutions whereas bases like sodium carbonate and buffers like the various sodium phosphates which produce more alkaline solutions. Test results confirm accepted wisdom that optimum bleaching occurs around the $pK_a$ for the peroxyacid, i.e. in the region of pH $8 \pm 0.5$ pH units, and that its effectiveness progressively increases from a pH such as 10 through 9 to 8. Consequently according to a further aspect of the present invention there are provided particulate compositions comprising at least 10% w/w MMSPB together with 1 or more solid pH regulators selected from inorganic acids or organic acids and one or more builders or buffers selected from alkaline phosphates, carbonates, silicates, borates amino carboxylates or phosphonates present in a total amount of at least 50% of the composition and in such relative amounts that the pH of a 1% solution in the range of from 7 to 8.5. Such compositions can readily be employed for washing, bleaching or disinfecting absorbent materials, hard surfaces, and aqueous media. Compositions directed more to disinfection are preferably buffered to provide a pH of 5 to 8.

The aforementioned compositions can be employed by themselves, or they can be employed in conjunction with surfactant-containing compositions or can be incorporated within such compositions. The nature of such other compositions will vary to some extent depending on the intended primary purpose of such compositions. Such compositions can be classified as general household washing compositions or sanitising/disinfecting compositions. General household washing compositions often contain at least 1% and in many cases from 5 to 95% and particularly from 5 to 40% by weight of one or more anionic, cationic, nonionic, zwitterionic, amphoteric or ampholytic surfactants, and in addition generally contain one or more builders in an amount from 1 to 90% and frequently from 5 to 70% by weight of the compositions, especially in a weight ratio to the surfactant of from 1:2 to 10:1. Such household washing compositions optionally can contain up to 40% by weight of a processing aid such as sodium or magnesium sulphate and optionally one or more auxilliary agents, often up to a total amount of not more than 20% of the composition, such as soil anti-redeposition agents, dye transfer inhibitors, optical brightening agents, per-oxygen stabilisers, corrosion inhibitors, bactericides, dyes, perfumes, foam enhancers, foam inhibitors, pH regulators, adsorbents, and abrasives. Such washing compositions tend to be employed in a weight ratio to the aforementioned MMSPB bleaching or sanitising compositions of 5:1 to 1:5. When the bleaching or sanitising compositions are incorporated within the washing composition, MMSPB are present in the total composition of not more than 40% and in many cases at least 0.5%. In general, by virtue of their activity, they are often present in an amount of not more than 10% w/w.

Representative surfactants can include soaps, alkyl benzene sulphonates, olefin sulphonates, linear alkane sulphonates, hydroxy-alkane sulphonates, alcohol sulphates, alkyl phenyl-ethylene oxide ether sulphates, tetra alkyl ammonium halides or pyridinium halides, condensed polyethylene oxide alkyl phenols or naphthols, fatty acid esters of polyols, polyglycols, amine oxides, phosphine oxides and suitably selected sulphonium and phosphonium amphoteric surfactants containing an anionic water-solubilising group.

Various of the suitable builders have been specified hereinbefore in conjunction with the bleach/sanitising composition. Amongst organic builders which are suitable herein as well as in the aforementioned bleaching compositions, which generally fall within the classes of alkaline salts of hydroxycarboxylic acids, polycarboxylic acids, amino polycarboxylic acids and polyphosphonic acids, particular mention should be accorded to sodium citrate, sodium salt of nitrilotriacetic acid and oxydisuccinic acid.

It will readily be understood that the aforementioned organic complexing agents can fulfil useful functions even when they are incorporated at low levels of, for example 0.1 to 5% w/w of the composition, i.e. at levels below the normally encountered builder levels. By so doing, the stability of the peroxygen compounds can be improved in use, and this can result in more efficient or improved bleaching. Many of such complexing agents satisfy the general formula:

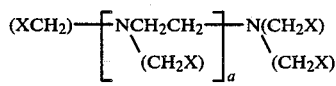

in which X represents a carboxylic acid or especially a phosphonic acid group or an alkali or alkaline earth metal salt thereof, such as sodium, potassium, calcium or magnesium salt or an ammonium salt and a represents either 0, 1 or 2, including EDTA, EDTMP, DTPA and DTPMP.

Amongst the auxiliary agents, sodium carboxymethylcellulose is of particular value as a soil antiredeposition agent and derivatives of diaminostilbene sulphonic acid and 1,3-diaryl-2-pyrazolines and aminocoumarins are typical optical brighteners. Proteolytic enzymes, if incorporated, are preferably coated with for example a non-ionic surfactant so as to minimise interaction with the peroxyacid salt. Amongst peroxyacid stabilisers there can be included such compounds as 8-hydroxy quinoline.

Any of the aforementioned invention washing composition can also contain if desired one or more inorganic persalts such as sodium perborate monohydrate or tetrahydrate or sodium percarbonate. Such persalts are often present in peroxyacid-free washing compositions up to 40% thereof, and when the MMSPB is incorporated, they can conveniently be present in a weight ratio of up to 5:1 thereto, the total of persalts and salt of peroxyacid preferably reaching no more than 40% of total composition. Compositions containing the persalt/peroxyacid mixture particularly benefit from incorporation of the low levels of especially amino phosphonic acid complexing agents, as referred to herein.

When considering sanitising/disinfecting compositions, it is common for the peroxyacid compositions to incorporate some additional component such as an alkali metal chloride or bromide, which in many cases comprises up to 70% of the total composition. Accordingly, such sanitising compositions can be regarded as a mixture of the aforementioned washing compositions containing peroxyacid with, in many cases, from 0.5 to 2 parts by weight of alkali metal chloride or bromide. In practice this leads to compositions comprising up to 40% of MMSPB, from 1 to 70% alkali metal chloride or bromide, from 0 to 50% of the surfactant, and from 0 to 70% of the builder. Within such formulations, MMSPB is preferably present in an amount from 5 to 20%, the alkali metal chloride or bromide is preferably present in an amount of at least 30%, the total builder including acidic component is preferably at least 10 to 50% and in practice often comprises from 5 to 30% of a phosphate builder and from 5 to 30% of a non-phosphate builder such as sodium carbonate or bicarbonate. Such compositions are particularly suited for the cleansing and sanitising of absorbent materials such as terry that has been soiled with human or animal waste products, especially from babies. One of more of the aforementioned auxilliary agents, generally in an amount of 5 to 20% of a total composition, as before, can likewise be included.

In practice, MMSPB is obtained in particulate form, and can be subsequently sieved, granulated, agglomerated or otherwise aggregated as necessary in order to produce particles generally within the range of 0.01 mm to 2 mm and especially from 0.05 mm to 1 mm, thereby to match to a reasonable extent the particle size ranges of other components in the compositions of which it is the peroxyacid-generating component. By so doing, it is possible to minimise problems of segregation which could otherwise arise during transportation and handling of the product.

The processes for washing articles according to the present invention can be carried out at a temperature from ambient temperature up to the boiling point of the washing solution. Compositions according to the present invention are particularly well suited to a process at which washing or bleaching is carried out by steeping at ambient or by heating the solution to a temperature from about 25° to 60°. Alternatively the washing and bleaching procsses may be effected by heating up a cold washing solution. A combination of processes can be used, such as cold steeping followed by a wash at 30°, 40° or 50° C. By virtue of the very rapid rate of dissolution of MMSPB in aqueous solution even at low wash temperatures, compositions containing such bleaching agents are particularly suitable for use at temperatures in the range of ambient temperature to 40° C., ambient often being regarded as about 25° C. Incorporation of an inorganic persalt, such as sodium perborate or percarbonate into MMSPB washing compositions imparts improved higher temperature wash capabilities so that the solution can be heated with advantage to hot wash conditions, i.e. often 80° to 90° C.

It is desirable for washing or bleaching solutions for use in the home to contain at least 1 part per million Avox and often at least 10 ppm Avox, from the percompound. Household washing solutions prepared by dissolution of detergent compositions in general provide no more than about 200 ppm. Avox., frequently no more than 100 ppm Avox.

As a general rule, the rate of removal of stains is enhanced by employing a higher temperature and by higher Avox. concentrations, but by virtue of the rapid rate at which MMSPB dissolve in water or aqueous detergent solutions, the contact period between solution and fabric can conveniently be as short as 5 minutes. Longer periods of for example, up to 1 hour tend to provide greater soil removal. In cold washing or steeping even longer periods can be employed, such as steeping overnight.

Many washing compositions are formulated so as to extract stains from fabrics into solution and to minimise the redeposition of such stains or dye transfer onto the fabric. Consequently, it is extremely desirable for the bleaching agent to be able to bleach stains in solution, and in this respect MMSPB are particularly useful on account of their comparatively high rate of solubility in aqueous alkaline solutions, thereby enabling the peroxyacidic species to be present in solution when the stains are extracted. However, even though MMSPB provide a more active bleaching species, damage to the dyestuffs in coloured fabrics is comparable with that caused by inorganic peroxygen compounds employed heretofore, and thus enables washing compositions containing MMSPB to be employed for coloured fabrics as well as for whites.

It will be fully recognised that the amount of washing composition containing MMSPB to employ in order to achieve such concentrations of Avox in the final solution is a function of the proportion of that percompound in either the washing composition or the bleaching composition employed in conjunction with some other washing composition. In practice, though, it is usual for the amount of percompound-containing washing composition to be employed at a concentration of from 0.5 gpl to 10 gpl and often from 0.8 gpl to 5 gpl, washing practices varying from country to country. When the bleach composition is used as an additive in conjunction with the washing composition or introduced separately into for example a subsequent rinsing stage, it is often employed at a concentration of from 0.3 to 4 gpl and in many instances from 0.5 to 2.5 gpl. Use outside these ranges is, of course, at the discretion of the user.

The sanitiser compositions are often employed in dilute aqueous solution and concentration of from 1 to 20 gpl. Fresh or replacement solution is often prepared at hand hot temperatures, typically 35° to 45° C., or higher temperatures could be employed if desired and thereafter either heated continuously or intermittently so as to maintain an elevated temperature or allowed to cool to ambient temperature whilst the solution is in contact with the articles to be sanitised. The solution can be partially or completely replaced periodically, commonly on a daily basis, and at the discretion of the user, the concentration of the sanitiser composition in solution can be augmented from time to time so as to restore the peroxyacid concentration to its former level. The articles to be sanitised are normally allowed to remain in solution for a considerable period of time, generally at least 4 hours and in many cases overnight or longer.

In processes for the disinfection/sanitising of aqueous media, such as recirculating water systems, such as in industrial cooling circuits, or effluents from food-processing industries, paper mills, sewage stations, or in potable or industrial water supplies, optionally chlorinated, the disinfection process can conveniently be effected by introducing the MMSPB together with any pH regulator or buffer as desired into the aqueous media particularly into employ pH generally in the region of from 5 to 9, and in general, sufficient of the salt is added to provide a concentration of at least 1 ppm MMSPB in the media often from 1 to 25 ppm. Use of the composition in such concentrations leads to a substantial reduction in the content of live microorganisms. In the event that the aqueous media contain oxidisable waste chemicals such as inorganic or organic cyanides and mercaptans and the like, at least one mole of MMSPB should be employed per mole of oxidisable substance. The pH of such media is preferably adjusted beforehand to and maintained at the known pH for safe peroxyacid reaction with such substances e.g. above pH 9 for cyanides.

In addition to washing and/or bleaching fabrics, the compositions can be used to clean hard surfaces such as metal, plastic or wooden surfaces, either by dissolving washing or bleaching compositions in water, preferably to provide 200 ppm to 2000 ppm avox especially 400 to 1000 ppm avox or by forming a slurry or paste of such compositions. Also, if desired, solutions produced by the dissolution of compositions described herein can be used to bleach textile fabrics, wood or pulp under the conditions, and employing the equipment used for bleaching such articles with hydrogen peroxide or inorganic peroxoacids.

Having described the invention in general terms, specific embodiments will be described more fully by way of example. Modifications to the following can be made by the skilled artisan without departing from the spirit of the invention.

THE EXAMPLES

1st Preparation of MMSPB 3-sulphobenzoic acid - sodium salt (5 g) was suspended in methanesulphonic acid (24 g) at 25° C. and aqueous hydrogen peroxide (4 g 70% w/w) was slowly introduced into the reaction mixture over 15 minutes. The mixture to be stirred at 30° C. for a total of 2 hours. The reaction mixture was then cooled by introduction of crushed ice (10 g) and a saturated solution of magnesium nitrate (25 ml of solution at ambient temperature) was then introduced, resulting slowly in the precipitation of a solid over 30 minutes. The precipitate was filtered off, pulled dry, and finally dried under vacuum over phosphorus pentoxide. The resultant crystalline product was obtained in a yield of 2.9 g and had an Avox content of 4.0% as O measured by the standard determination using potassium iodide and titration of the liberated iodine using sodium thiosulphate. The theoretical yield would have been 4.77 g and theoretical Avox of 6.99%. The magnesium content was 4.7% compared with a theoretical content of 5.24%. Examination of the infra-red spectrum revealed peaks at 1750 cm$^{-1}$ and between 1150 and 1250 cm$^{-1}$ but only a minor peak at 1700 cm$^{-1}$ demonstrating the existence of the peroxycarboxylic acid and sulphonate groups and a minor amount of carboxylic acid groups respectively.

2nd Preparation of MMSPB

Benzoic acid (5 g) was suspended in sulphuric acid (20 g, 98% w/w) and heated to 200° C. using an oil bath. After 2 hours at 200° C., the reaction mixture cooled to 20° C. and concentrated hydrogen peroxide (4 g, 70% w/w) introduced with stirring over a period of 15 minutes, the temperature being maintained below 25° C. The mixture was stirred for a further hour at 40° C. and then cooled to 20° C. Crushed ice (10 g) was added and the solution went clear. Saturated magnesium nitrate solution (25 ml) was then stirred in and a precipitate developed over the subsequent 30 minutes. The solids were filtered off and vacuum dried over phosphorous pentoxide. The yield was 2.4 g of product having an avox content of 4.42% and a magnesium content of 4.85%. The IR spectrum was substantially the same as for the first preparation route.

3rd Preparation of MMSPB

To a suspension of 3-sulphobenzoic acid (5 g, $2.5 \times 10^{-2}$ moles) in dichloromethane (60 ml) containing a trace of sulphuric acid ($5 \times 10^{-5}$ moles) was slowly added hydrogen peroxide (3 g; 85%). The suspension was boiled under reflux (42° C.) for 1 hour after which it was cooled to room temperature, the dichloromethane was decanted off and the residue treated with saturated aqueous magnesium nitrate (25 ml). The resultant precipitate was filtered off, dried over phosphorous pentoxide under vacuum to yield the magnesium salt of 3-sulphoperoxybenzoic acid (3.5 g; 5.31% Avox as O; Magnesium content of 4.7%) compared with a theoretical yield of 5.67 g. The IR spectrum was again substantially the same as for the other preparations.

Compositions containing MMSPB

| | Biocidal Formulations | | |
|---|---|---|---|
| BO1 | % w/w | BO2 | % w/w |
| MMSPB (4.4% Avox) | 13.2 | MMSPB | 14 |
| LAS | 7.0 | LAS | 7 |
| Boric Acid | 5.0 | Sodium carbonate | 23 |
| NaH$_2$PO$_4$ | 10.0 | sodium tripolyphosphate | 10 |
| Corrosion Inhibitor | 1.0 | | |
| Perfume | 0.5 | sodium chloride | 46 |
| Na$_2$SO$_4$ | 63.3 | | |

Doseage of 1 gpl of either formulation would provide about 6 ppm Avox.

| Bleaching Formulation | | | |
|---|---|---|---|
| | % w/w Composition in | | |
| Ingredient | BL1 | BL2 | BL3 |
| MMSPB | 9.1 | 36.5 | 63.5 |
| Surfactant | 4.0 | 4.0 | 4.0 |
| Optical Brightening Agent | 0.1 | 0.1 | 0.1 |
| Boric acid | 10.0 | 10.0 | 10.0 |
| Sodium Sulphate | 78.3 | 49.4 | 22.4 |

| Detergent Base Formulations | | | |
|---|---|---|---|
| Ingredient | % w/w Composition at | | |
| | DB1 | DB2 | DB3 |
| MMSPB | 7.6 | 13.2 | 18.9 |
| Boric Acid | 10.0 | 10.0 | 10.0 |
| Sodium tripolyphosphate | 29.5 | 22.6 | 16.9 |
| Na$_2$SO$_4$ | 14.0 | 14.0 | 14.0 |
| NaSiO$_3$ | 14.0 | 14.0 | 14.0 |
| LAS | 7.0 | 7.0 | 7.0 |
| Non-ionic surfactant | 5.1 | 5.1 | 5.1 |
| Soap | 6.4 | 6.4 | 6.4 |
| EDTA | 0.13 | 0.13 | 0.13 |
| CMC | 1.0 | 1.0 | 1.0 |
| Optical Brightener | 0.13 | 0.13 | 0.13 |
| H$_2$O | | balance | |
| | DB4 | DB5 | DB6 |
| LAS (E11.5) | 7.0 | 6.0 | 6.0 |
| Tallow alcohol ethoxylate (14EO) | 2.5 | 6.0 | 7.0 |
| Sodium Soap (C 18) | 3.0 | 3.0 | 2.0 |
| Sodium tripolyphosphate | 40.0 | 30.0 | 30.0 |
| Sodium silicate | 6.5 | 5.0 | 5.0 |
| Magnesium silicate | 1.5 | — | — |
| Boric acid | — | 6.0 | 8.5 |
| CMC | 1.0 | 1.0 | 1.0 |
| EDTA-Na$_2$ | 0.2 | 0.2 | 0.2 |
| OBA | 0.2 | 0.2 | 0.2 |
| Na$_2$SO$_4$ | 16.5 | 23.5 | 16.0 |
| MMSPB | 13.0 | 11.0 | 7.0 |
| PBS monohydrate | — | — | 9.0 |
| Perfume | 0.1 | 0.1 | 0.1 |
| Water (bound) | | balance | |

Performance

The washing performance of MMSPB was tested by washing swatches of cottom cloth which had been prestained with red wine at 40° C. for 10 minutes and 20 minutes respectively in the presence of a detergent composition at 6 gpl which analysed as follows:

| % w/w | |
|---|---|
| 45.8 | STPP (Na$_5$P$_3$O$_{10}$) |
| 14.0 | Na$_2$SO$_4$ |
| 14.0 | Na$_2$SiO$_3$ |
| 7.0 | L.A.S (Linear alkyl benzene sulphonate) |
| 5.1 | Non-ionic surfactant |
| 6.4 | Soap |
| 0.13 | EDTA |
| 1.0 | C.M.C (Carboxymethyl cellulose) |
| 0.13 | Optical brightening agent |
| balance | Water |

The water had a hardness of 250 ppm, in a calcium/magnesium weight ratio of 3:1. The MMSPB provided an Avox in solution of 35 ppm.

The trials were carried out in a laboratory scale washing machine sold under the name TERGOTOMETER (Trade Mark) by the US Testing Corporation which simulates the action of a vertical agitator type domestic washing machine. After being washed, each swatch was rinsed with cold water and hot air dried. The reflectance of each swatch was determined after washing ($R_f$) and compared with its pre-washed reflectance ($R_i$) and that of the unstained cloth ($R_u$) giving a measure of stain removal, using an instrumental colour system MICROMATCH reflectance spectrophotometer equipped with a xenon light lamp light source and a D65 filter to approximate to CIE artificial daylight. An average of 4 reflectance readings were taken for each swatch backed by three thicknesses of unstained material. The percentage stain removal was obtained using the formula percentage:

$$\% \text{ stain removal} = 100 \times (R_f - R_i)/(R_u - R_i).$$

The results are summarised in Table 3 below.

TABLE 3

| Bleach | pH | % Stain Removal | |
|---|---|---|---|
| | | 10 Mins | 20 Mins |
| MMSPB | 8 | 75.2/79.1 | 77.1/81.3 |
| MMSPB | 9 | 68.6/67.2 | 73.3/70.2 |

From Table 3 above, it will be recognised that the performance of MMSPB is sensitive to changes in pH and that at or near pH 8, it is an extremely effective stain remover.

By way of comparison, when the corresponding washing trials were carried out using the magnesium salt of the 2-sulphoperoxybenzoic acid, under identical conditions, there was no substantial soil removal attributable to the peroxyacid at all, removals at pH 8 or 9 being substantially the same and not exceeding 30% even after 20 minutes. These results, therefore, demonstrate clearly the markedly better performance of the MMSPB in comparison with the 2-sulphoperoxybenzoic acid salts.

We claim:

1. In solid form, a salt, expressed in anhydrous form, having the general formula:

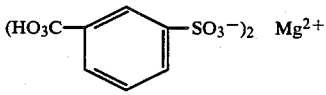

2. A process for the manufacture of the monomagnesium salt of 3-sulphoperoxybenzoic acid comprising reacting a suspension of the corresponding salt of 3-sulphobenzoic acid or salt thereof in the presence of a strong acid with concentrated hydrogen peroxide until at least some of the carboxylic acid groups have been peroxidised at a temperature selected in the range of ambient to 60° C., precipitating the monomagnesium salt of 3-sulphoperoxybenzoic acid, and separating the precipitate from its mother liquor.

3. A process according to claim 2 in which the mole ratio of hydrogen peroxide to the 3-sulphobenzoic acid or salt thereof is selected in the range of 1.2:1 to 5:1.

4. A process according to claim 2 in which the reaction is effected at a temperature of 30° C. to 45° C.

5. A process according to claim 2 in which the reaction period/residence time is from half an hour to four hours.

6. A process according to claim 2 employing hydrogen peroxide having a concentration of at least 70% w/w.

7. A process according to claim 2 in which the reaction mixture is cooled by at least 15° C.

8. A process according to claim 2 in which the mole ratio of hydrogen peroxide to the 3-sulphobenzoic acid or salt thereof is selected in the range of 1.2:1 to 5:1 and the reaction is effected at a temperature of 30° C. to 45° C. during a reaction period/residence time of from half an hour to four hours.

9. A process according to claim 2 or 8 in which the magnesium nitrate is introduced as a substantially saturated aqueous solution.

10. A process according to claim 2 or 8 in which the 3-sulphobenzoic acid or salt thereof is suspended in sulphuric acid or methanesulphonic acid in a mole ratio of the former to the latter of not less than 1:20.

11. A process according to claim 10 in which the suspension is obtained by reacting benzoic acid with sulphuric acid in a mole ratio of the former to the latter of from 1:3.5 to 1:20, so as to form 3-sulphobenzoic acid in a sulphuric acid.

12. A process according to claim 2 or 8 in which the reaction medium comprises either a hydrocarbon or halogenated hydrocarbon or mixtures thereof, providing a boiling point for the medium within the respective specified temperature range in claim 2 or 4, and containing at least a catalytic amount of the strong acid.

13. A process according to claim 12 in which the cation medium comprises pentane and/or dichloromethane.

14. A desensitised peroxygen composition comprising magnesium 3-sulphoperoxybenzoic acid, hereinafter MMSPB, in intimate contact with a solid diluent in an amount of at least half the weight of MMSPB.

15. A bleach composition comprising a buffering agent or pH regulator and MMSPB, in such relative amounts that a 1% solution of the composition in water has a pH of 7 to 8.5.

16. A washing composition comprising a surfactant and at least 0.5% w/w MMSPB.

17. A washing composition according to claim 16 containing at least 1% surfactant, at least 1% builder, up to 40% processing aid, up to 20% detergent auxiliary agents and 0.5 to 10% MMSPB.

18. A sanitising composition comprising 1% to 70% alkali metal chloride or bromide, 0.5% to 40% MMSPB, 0 to 50% surfactant, and 0 to 20% builder.

19. A composition according to any one of claims 14 to 18 or 24 which additionally contains from 0.1 to 5% w/w of a complexing agent that satisfies the general formula:

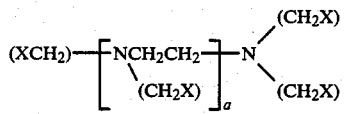

in which X represents a carboxylic acid or a phosphonic acid group or an alkali or alkaline earth metal salt thereof, and in which a represents 0, 1 or 2.

20. A process according to claim 2 wherein precipitation is effected by cooling the reaction mixture.

21. A process according to claim 2 wherein precipitation is effected by augmenting the concentration of metal ions in solution.

22. A process according to claim 21 wherein the concentration of metal ions in solution is augmented by introducing magnesium nitrate into said solution.

23. A composition according to claim 16 which further contains at least 40% w/w of a persalt.

* * * * *